(12) United States Patent
Robinson et al.

(10) Patent No.: US 6,766,698 B1
(45) Date of Patent: Jul. 27, 2004

(54) METER SOCKET JAW TESTER APPARATUS AND TEST METHOD

(75) Inventors: Darrell Robinson, Highland, MI (US); Karl R. Loehr, Commerce Township, MI (US)

(73) Assignee: Ekstrom Industries, Inc., Farmington Hills, MI (US)

( * ) Notice: Subject to any disclaimer, the term of this patent is extended or adjusted under 35 U.S.C. 154(b) by 16 days.

(21) Appl. No.: 10/161,364

(22) Filed: Jun. 3, 2002

(51) Int. Cl.⁷ ................................................ G01N 3/02
(52) U.S. Cl. .......................................... 73/856; 439/839
(58) Field of Search .................. 73/855, 856; 439/839, 439/517

(56) References Cited

U.S. PATENT DOCUMENTS

| | | | | |
|---|---|---|---|---|
| 4,135,101 A | * | 1/1979 | Young et al. .................. | 307/39 |
| 5,120,252 A | * | 6/1992 | Mayo et al. ................... | 445/22 |
| 5,334,057 A | * | 8/1994 | Blackwell .................... | 439/839 |
| 5,546,269 A | * | 8/1996 | Robinson et al. ............ | 361/660 |
| 6,152,764 A | * | 11/2000 | Robinson et al. ............ | 439/517 |
| 6,325,666 B1 | * | 12/2001 | Robinson et al. ............ | 439/517 |
| 6,409,537 B2 | * | 6/2002 | Robinson et al. ............ | 439/517 |
| 6,428,350 B1 | * | 8/2002 | Robinson et al. ............ | 439/517 |
| 6,443,761 B1 | * | 9/2002 | Robinson et al. ............ | 439/517 |
| 6,478,589 B2 | * | 11/2002 | Robinson et al. ............ | 439/146 |
| 6,488,535 B1 | * | 12/2002 | Robinson et al. ............ | 439/517 |
| 6,520,798 B1 | * | 2/2003 | Robinson et al. ............ | 439/517 |
| 6,549,388 B2 | * | 4/2003 | Robinson | |

* cited by examiner

*Primary Examiner*—Edward Lefkowitz
*Assistant Examiner*—Andre Allen
(74) *Attorney, Agent, or Firm*—Young & Basile, PC (57) ABSTRACT

A jaw contact tester and conditioning apparatus for measuring push-in and pull-out forces between a blade terminal and a jaw contact mounted in an electrical power service apparatus. The jaw contact tester is provided in multiple aspects providing, in one aspect, a simple go/no-go pull-out force indication, in a second aspect providing a push-in and pull-out force indication on separate scales carried on the tester and, in a third aspect, allows a force measurement gauge to be attached to the blade terminal holder for measuring blade push-in and blade pull-out forces relative to a jaw contact.

22 Claims, 10 Drawing Sheets

METER SOCKET JAW TESTER APPARATUS AND TEST METHOD

BACKGROUND

The present relates, in general, to watthour meter sockets and watthour meter socket adapters and, more specifically, to watthour meter socket and socket adapter jaws contacts.

In the electric utility industry, plug-in, socket-type watthour meters are commonly employed to measure electrical power consumption at a residential or commercial building establishment. A cabinet is typically mounted on an outside wall of the residence or building and contains a meter socket having pairs of line and load contacts which are connected to electric power line conductors extending from the utility power network and electric load conductors connected to the residential or building establishment power distribution network. The contacts receive blade terminals on a plug-in watthour meter to complete an electric circuit through the meter between the line and load terminals mounted in the cabinet for the measurement of electrical power consumption.

S-type, socket-type, plug-in watthour meters have replaced older A base bottom connected meters which were formed of a single piece housing in which the watthour meter was fixedly mounted along with compression terminals which provide connection to the utility power lines and the building load distribution network.

In an installation involving an A-type bottom connected meter, an A to S socket adapter is used to allow a new S-type watthour meter to be installed. The socket type meter has outwardly extending blade terminals which are insertable into the jaw contacts in the cabinet of an S-type meter socket. The socket adapter includes its own set of female jaw contacts which receive the male blade terminals of the S-type plug-in, socket-type meter.

The jaw contacts employed in the watthour meter socket and watthour meter socket adapter may take many different forms including a folded over contact structure as well as a blade and spring clip structure. Regardless of the structural arrangement of the jaw contact, each jaw contact in a watthour meter socket adapter or watthour meter socket must provide a secure electrical connection to a blade terminal inserted therein as well as enabling the blade terminal to be both easily inserted into and removed from the jaw contact to function with a plug-in watthour meter or watthour meter socket adapter.

Thus, jaw contacts are designed to meet certain minimum push-in and pull-out force requirements, such as twenty-five pound push-in force and a seven and one half pound pull-out force. These force requirements enable a jaw contact in a watthour meter socket or watthour meter socket adapter to meet the dual functions of easy insertion and replacement of a watthour meter or socket adapter and providing a secure electrical connection to the blade terminal inserted therein over the typically long service life of a watthour meter socket or watthour meter socket adapter. However, there is no known tester for jaw contacts used in a watthour meter socket adapter or watthour meter socket which is capable of measuring the push-in and/or pull-out forces generated by a jaw contact on a blade terminal.

Despite the fact that there has been no known tester for jaw contacts to measure the push-in or pull-out forces generated by a jaw contact on a blade terminal, it is known that the push-in and pull-out forces vary practically from jaw contact to jaw contact despite tight manufacturing process controls. It would be desirable to have a jaw contact conditioner which can be easily inserted into a jaw contact, typically after the jaw contact is mounted in a watthour meter socket or socket adapter/extender, and pushed into and pulled out of the jaw contact several times to condition the jaw contact for the insertion of a meter blade terminal therein by relaxing or opening the jaw contact jaws a minute amount to thereby bring the push-in forces closer to specifications.

The Assignee of the present invention has previously employed a standard jaw blade terminal fixed, such as by welding, on the end of a long handle-like screwdriver as a jaw conditioner. However, it is believed that further improvements may be made to a jaw contact conditioner to adapt the conditioner to also function as a blade terminal/jaw contact push-in and pull-out force measurement device.

SUMMARY

The present invention is a jaw contact tester and jaw contact conditioner useful in measuring blade terminal push-in and pull-out forces relative to a jaw contact mountable in an electrical power service apparatus. In a first aspect of the present invention, a jaw contact tester apparatus is disclosed for testing the pull-out force of a jaw contact in an electrical device, such as a watthour meter socket or a watthour meter socket adapter. The tester comprises a housing having first and second opposed ends, with the first end is displaceable relative to the second end. A blade is fixedly mounted within the housing and is extendable through the first end of the housing into relatable engagement with the jaw contact upon engagement of the first end of the housing with the jaw contact. Biasing means are disposed in the housing for exerting a force between the first and second ends of the housing tending to separate the blade from a jaw contact when the blade is mounted in a jaw contact. The biasing means will cause the blade to disengage from the jaw contact only when the force exerted by the biasing means on the housing engaged with the jaw contact exceeds the pull-out force resistance of the jaw contact on the blade.

In this aspect, the housing preferably includes a first housing portion and a second housing portion, the first housing portion being telescoping arranged relative to the second housing portion. A slot is formed in the first end of the first housing portion for slidable extension of the blade therethrough. The biasing means is disposed between the first end of the first housing and a support mounted within the first and second housing portions and fixedly connected to the second housing.

In another aspect, the jaw contact tester includes a housing having an aperture at one end. A slider is movably disposed within the housing and has an end formed as a blade terminal slidingly extendible through the aperture in the housing into releasable engagement with a jaw contact in an electrical apparatus. A first plunger is carried by the slider for movement in one direction and displaceable from the slider upon movement of the slider in an opposite direction. Biasing means are coupled to the slider for biasing the slider in a direction to retract the first end of the slider toward the housing. A first indicator is carried by the first plunger and extends through an aperture in the housing adjacent to a scale means on the housing for indicating the force required to move the blade terminal relative to the jaw contact.

A second plunger may also be mounted from the housing. A second indicator is carried by the second plunger and extends through a second aperture in the housing for displacement relative to a second scale means carried on the housing. The second plunger is operable by movement of the slider in an opposite direction.

The first and second plungers are separable from the slider upon movement of the slider in opposite directions.

In another aspect of the invention, jaw contact tester is in the form of a blade holder having a blade mountable on and extending from one end of the holder. Means are formed on the second end of the holder for receiving a coupler attachable to a force measurement device, such as a force measurement gauge. In one aspect, an open ended slot is formed at the other end of the holder body and receives a transversely mounted pin. A hook is attachable to the force measurement device and the pin to measure blade pull-out force relative to a fixed jaw contact.

In another aspect, a threaded coupler is attachable to the force measurement device and is threadingly engagable in a threaded bore formed in the other end of the holder body to attach the force measurement device to measure at least one of, and preferably, both of the blade push-in and blade pull-out forces relative to a stationery jaw contact.

The jaw contact testers and conditioners of the present invention provide a unique means for measuring blade push-in and/or pull-out forces relative to a stationary jaw contact mountable in an electrical power service apparatus, such as a watthour meter or watthour meter socket adapter/extender.

The jaw contact testers may be constructed in different versions to provide a simple go/no-go blade pull-out force test. Alternately, the blade holder itself may be provided with force measurement scales to provide an indication of one or both of blade push-in and blade pull-out forces. Further, a force measurement device, such as a force gauge, is attachable to the blade holder to measure blade push-in and pull-out forces.

BRIEF DESCRIPTION OF THE DRAWING

The various features, advantages and other uses of the present invention will become more apparent by referring to the following detailed description and drawing in which.

DETAILED DESCRIPTION

Figure 14:
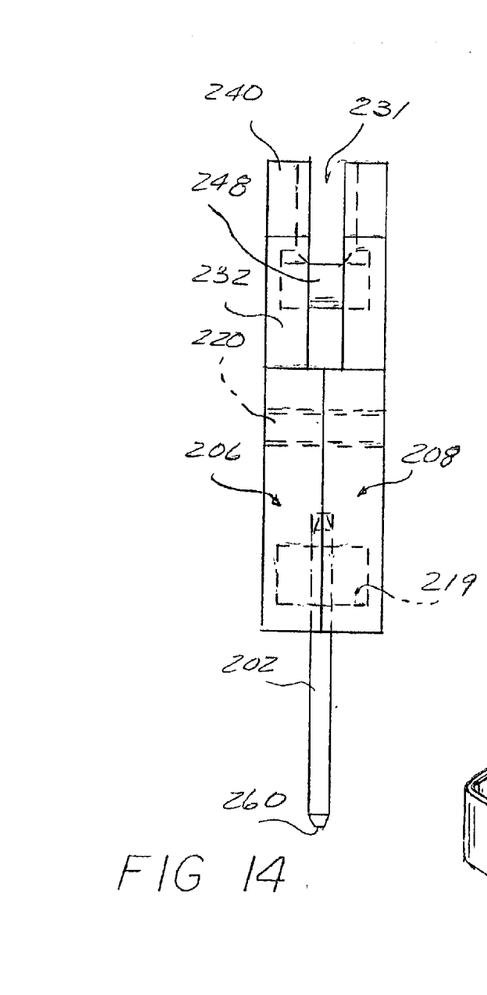
FIG. 14 is a plan elevational view of the jaw contact tester and conditioner shown in FIGS. 12 and 13.

Refer now to the drawing, and to FIG. 14 in particular, there is depicted one aspect of a jaw contact tester 10 suited for providing an indication of a minimum jaw contact pull-out force on separation of a blade terminal from the jaw contact. The jaw contact tester 10 may be formed of any suitable material. Preferably, a light weight material, such as a metal or plastic, with polyvinyl chloride (PVC) being preferred, is used to form most of the components of the jaw contact tester 10 except for the blade terminal, biasing spring and interconnecting pins and fasteners.

Figure 1:
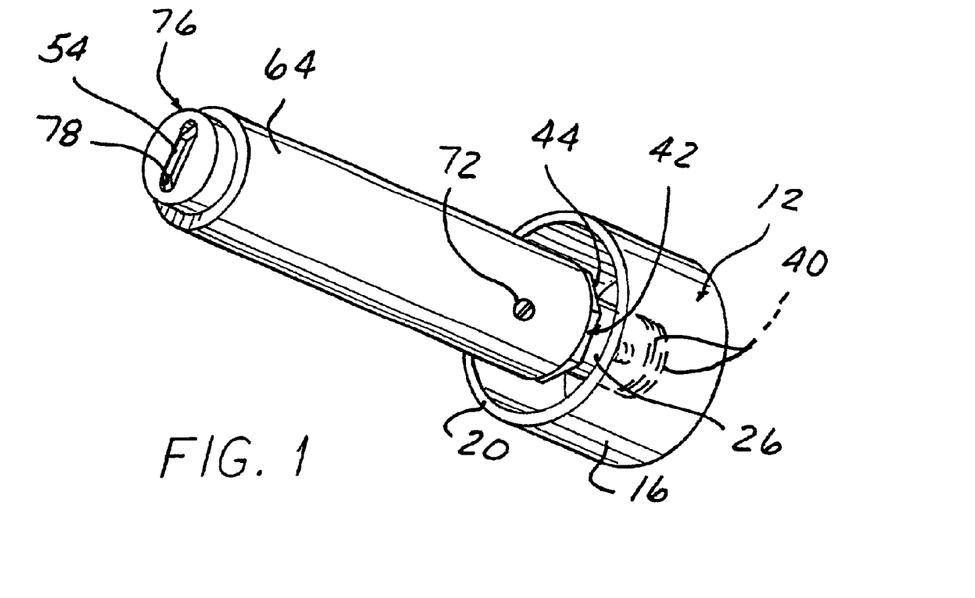
FIG. 1 is a perspective view of a jaw contact tester constructed in accordance with one aspect of the present invention.
Figure 2:
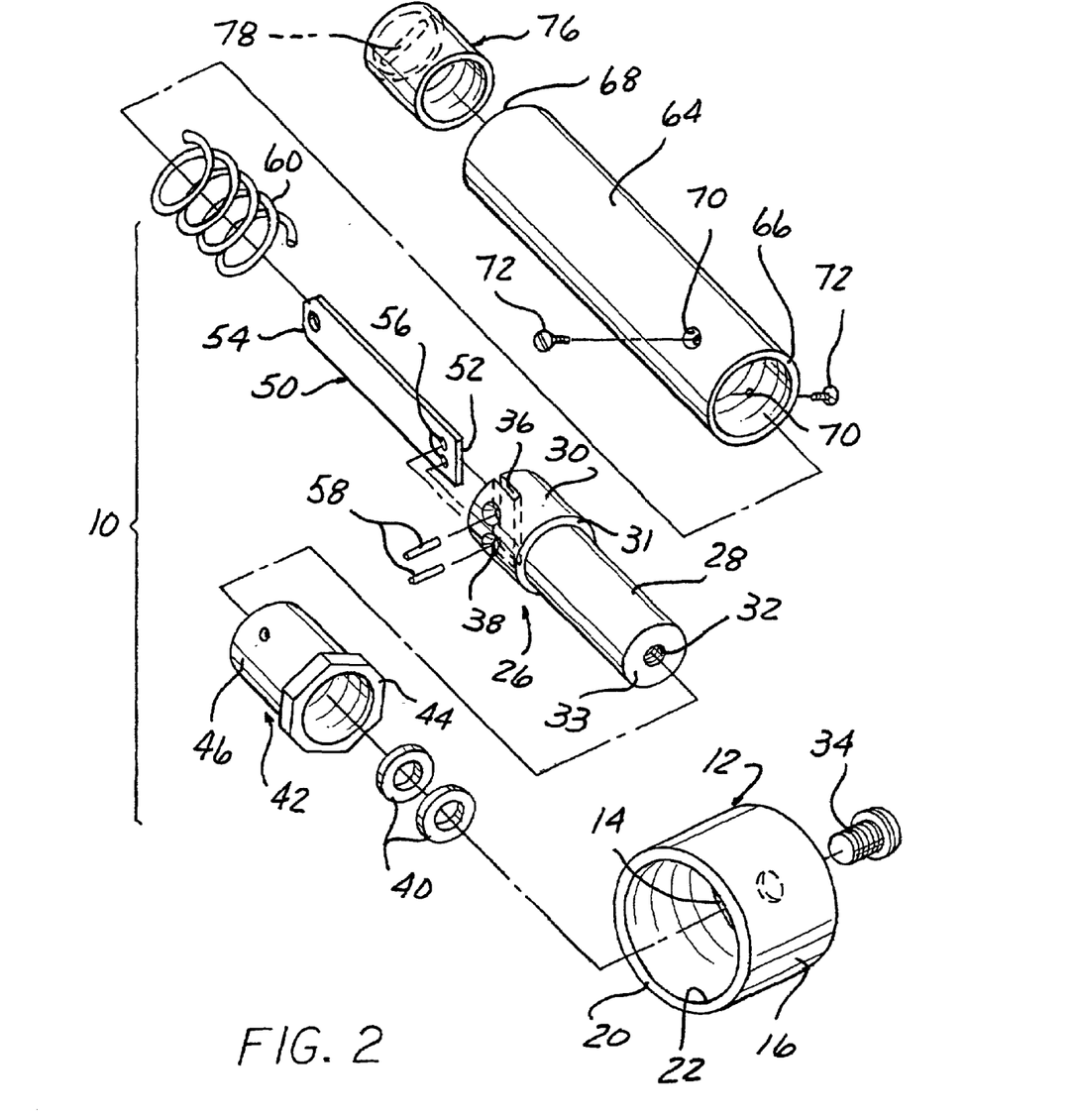
FIG. 2 is an exploded, perspective view of the jaw contact tester depicted in FIG. 1.
Figure 3:
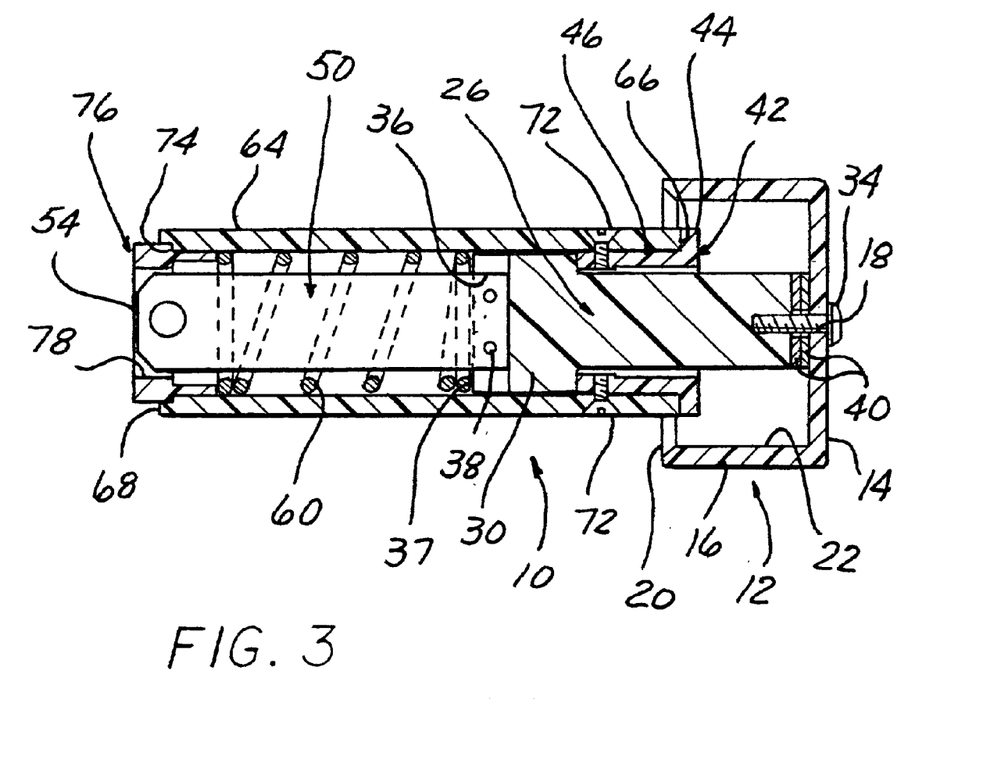
FIG. 3 is a cross-sectional view of the jaw contact tester shown in FIG.

As shown in FIGS. 1–3, the jaw contact tester 10 includes a base 12.

The base 12 may have any desired configuration, with the depicted cylindrical configuration being shown by example only. The base 12 includes a central wall 14 and a side wall 16 which, in the case of a cylindrical base 12, has a generally annular form. An aperture 18 is formed in the end wall 14 for receiving a fastener therethrough, as described hereafter. The sidewall 16 projects from the end wall 18 to an open end 20 thereby defining a hollow interior cavity 22.

A support 26 is mounted in the base 12 and projects axially from the end wall 14 of the base 12. The support 26 has an elongated, generally cylindrical shape formed of a first smaller diameter shank 28 and an enlarged diameter end portion 30. It will be understood that this configuration is depicted by way of example only as the support 26 may have other configurations, such as a constant diameter cross-section or a non-circular cross-section. A threaded bore 32 is formed in a first end 33 of the shank 28 for receiving a fastener, such as a screw 34, which projects through the aperture 18 and the end wall 14 of the base 12 into the threaded bore 32.

An annular shoulder 31 is formed between the shank 28 and the enlarged diameter end portion 30 for reasons which will become more apparent hereinafter. A slot like aperture 36 is formed in the end 37 of the end portion 30 of the support 26 for receiving a blade terminal as described hereafter. At least one and, preferably, a pair of apertures 38 extend transversely through the enlarged diameter end portion 30 intersecting the slot 36.

One or more centering members or discs, such as washers 40, are interposed between the first end of the shank 28 and the end wall 14 of the base 12, as shown in FIG. 3. The centering members have a larger diameter than the diameter of the shank 28 so as to extend radially outward from the shank 20 as also shown in FIG. 3.

The centering discs 40 support a spacer 42 relative to the shank 28 of the support 26. The spacer 42 also has a generally cylindrical configuration with a first end 44 adapted to seat against the end wall 14 of the base 12 and an elongated sidewall 46 projecting from the end wall 44. The diameter of the end wall 44 is larger than the diameter of the sidewall 46 for reasons which will become more apparent hereafter.

It should be noted that the length of the sidewall 46 of the spacer 42 determines the amount or length of insertion of the second end 54 of the blade 50 into the jaw contact as well as the amount of compression of the biasing means or spring 60 and thereby the amount of pull-out force exerted on the blade 50 to attempt to pull the blade 50 out of engagement with the jaw contact. Spacers having different length sidewalls 46 may also be employed to vary the length of insertion of the blade 50 into a jaw contact and/or to vary the spring force exerted by the biasing means 60 to attempt to pull the blade 50 out of the jaw contact.

A blade 50 has a first end 52 and an opposed second end 54. The blade 50 has an elongated, generally planar extent between the first and second ends 52 and 54. The second end 54 is shaped as a blade terminal commonly issued in watthour meters and watthour meter socket adapters and is configured and sized for removable insertion into a conventional watthour meter socket or watthour meter socket adapter jaw contact, as described hereafter and shown in FIG. 4. The blade 50 is formed of a conventional conductive material, such as plated copper.

A pair of apertures 56 are formed in the blade 50 adjacent the first end 52 and are alignable with the apertures 38 in the end portion 30 of the support 26. The aligned apertures 38 and 56 receive a suitable fasteners, such as roll pins 58. The roll pins 58 securely mount the blade 50 in the slot 36 in the large diameter end portion 30 of the support 26, with the blade 50 extending generally coaxially from the support 26.

A biasing means, such as a coil spring 60 is disposed about the blade 50 and seats at one end against end of the enlarged diameter end portion 30 of the support 26, An opposite end of the spring 60 seats against an end cap, described hereafter, when the blade 50 is inserted into a jaw contact.

The biasing means or spring 66 is selected to provide a predetermined spring force, such as seven and one half pounds, by way of example only. Different springs with different spring forces may also be employed to vary the pull-out force provided by the jaw contact tester 10 as described hereafter.

A cylindrical sleeve 64 is disposed about the blade 50 and has opposed first and second ends 66 and 68. The inner diameter of the sleeve 64 is sized to slidably fit over the enlarged diameter end portion 30 of the support 26. A pair of transverse bores 70 are formed in the sleeve 64 adjacent the first end 66 and receives set screws 72 therethrough. The set screws 72 are positioned to engage the shoulder 31 on the support 26 to act as a limit to the amount of axial extension of the sleeve 64 relative to the base 12. However, the sleeve 64 is freely moveable in an opposite axial direction toward the end wall 14 of the base 12.

The second end 68 of the sleeve 64 is notched to form an annular interior recess 74 designed to receive an end cap 76. The end cap 76 has a cylindrical configuration with the diameter sized to fit within the recess 74. Fastening means are employed to fixedly mount the end cap 76 in the second end 68 of the sleeve 64. A slot-like aperture 78 is formed in an end of the end cap 76 for passage of the second end 54 of the blade 50 therethrough.

The outer diameter of the sleeve 64 is smaller than the inner diameter of the annular side wall 16 of the base 12 to enable the first end 66 of the sleeve 64 to telescope within the sidewall 16 of the base 12 during operation of the jaw contact tester 10 as described hereafter.

FIG. 3 depicts the sleeve 64, the biasing means or spring 60 and the blade 50 at a nominal rest position with respect to a jaw contract. As shown in FIG. 3, the end 54 of the blade 50 is situated within the confines of the slot 78 in the end cap 76. The second end 54 of the blade 50 could also extend slightly outward from the end cap 76.

Figure 4:
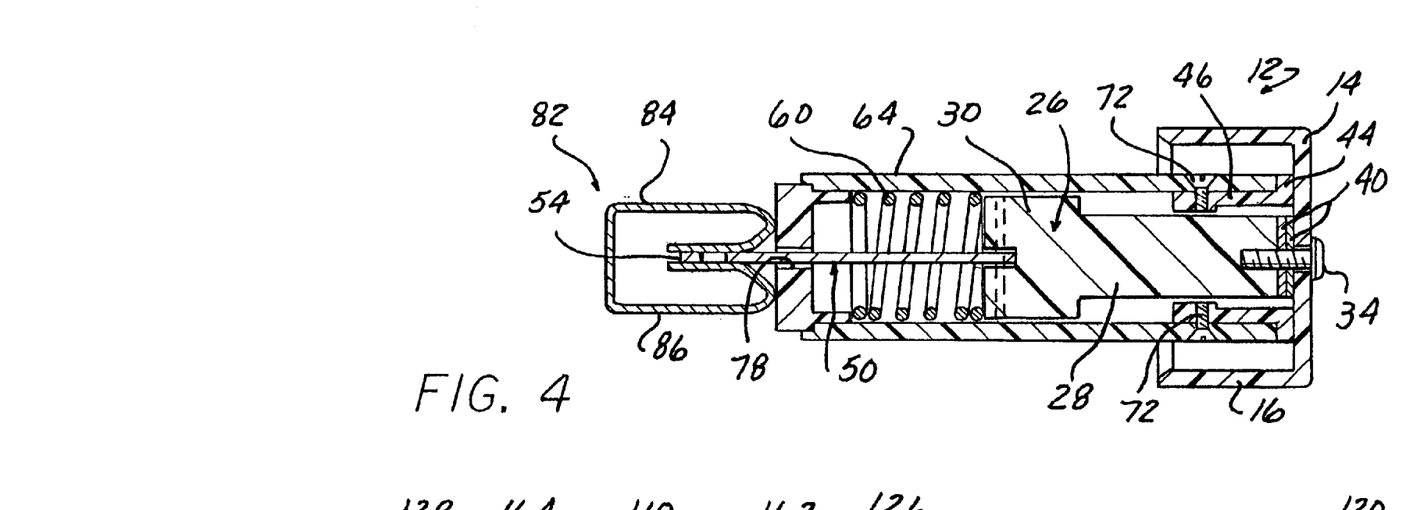
FIG. 4 is a side cross-sectional view generally similar to FIG. 3; but showing the components of the jaw contact tester in a pull-out test position.

In operation, as shown in FIG. 4, the end wall of the end cap 76 is brought into engagement with the outer ends of a jaw contact 82 typically formed of first and second resiliently spaced jaws 84 and 86. Force is exerted on the base 12 causing a relative movement of the blade 50 and the support 26 relative to the sleeve 64. This relative movement results in a telescoping, sliding movement of the sleeve 64 over the support 26 in the direction of the end wall 14 of the base 12 and a simultaneous extension of the second end 54 of the blade 50 through the aperture 78 in the end cap 76 and into engagement with the jaws 84 and 86 of the jaw contact 82. During such telescoping movement, the spring 60 is compressed. When the insertion force is released from the base 12, the compressed force of the spring 60 urging the spring 60 in an axially opposed direction causes opposite relative movement between the support 26 and the blade 50 relative to the end cap 76 and sleeve 64. Such relative movement within a direction axially away from the jaws 84 and 86 of the jaw contact 82 tends to pull on the blade 50 in a direction to disengage the blade 50 from the jaws 84 and 86 of the jaw contact 82. Since the spring 60 has been selected to provide a spring force of approximately seven and one half pounds, a seven and one half pound force is exerted on the blade 50 to attempt to disengage the blade 50 from the jaws 84 and 86. If the jaw contact 82 has a sufficient pull-out force resistance, the jaw contact 82 will exert a counter force greater than the force exerted by the spring 60 on a blade 50 and will retain the blade 50 between the jaws 84 and 86. However, if the pull-out force resistance of the jaw contact 82 is less than the prescribed pull-out force of seven and one half pounds, in the instant example, the spring 60 will overcome the retention force exerted by the jaws 84 and 86 on the blade 50 and will successfully disengage the blade 50 from the jaws 84 and 86.

The above-described jaw contact tester 10 provides a quick and easy test of the pull-out force of a jaw contact. The jaw contact tester 10 of the present invention is easy to use and provides a go/no-go test since the blade 50 in the jaw contact tester 10 either remains within the jaw contact 82 or is successfully disengaged therefrom by the spring 60 within the jaw contact tester 10. Further, the tester 10 can be used to condition a new jaw contact by repeated insertions and removals to loosen the jaw contact for subsequent use.

Referring now to FIGS. 5–11, there is depicted another aspect of a jaw contact tester 100 according to the present invention. The jaw contact tester 100 is formed of a housing 112 formed of a first and second separable housing portions or halves 114 and 116, respectively. Each of the first and second housing portion 114 and 116 generally comprises a semi-circular member having a generally elongated, semi-circular shape between opposed first and second ends 118 and 120 for the first housing portion 114 shown in FIGS. 7–11.

The housing 112 is formed of a suitable light weight material, such as a plastic. By example, polyvinyl chloride (PVC) can be employed to form the housing 112.

The first and second housing portions 114 and 116 are substantially identical except that the first housing portion 114 has axially aligned first and second slots 122 and 124 that extend completely through the housing portion and a pair of internal stops, as described hereafter. The first and second housing portions 114 and 116 may be joined together by any suitable means, such as by adhesive or releasable fasteners, such as screws.

First and second graduated scales 126 and 128 are formed on the first housing portion 14 adjacent to the first and second slots 122 and 124, respectively. The first and second scales 126 and 128 are useable with a pointer or indicator, as described hereafter, to provide an indication of the amount of push-in and pull-out force exerted by a jaw contact engaged with a blade mounted within the housing 112 of the jaw contact tester 110.

As shown in FIGS. 7–11, a slider 130 is movably disposed within bores formed in the mating first and second housing portions 114 and 116. The slider 130 may be formed of a suitable material, with metal being preferred; although high strength plastics may also be employed.

The slider 130 has a first end 132 slidably extendible through an aperture 133 formed at the first end 118 of the housing 112 and an opposed second end 134 mounted internally within the housing 112. A plurality of axially spaced slots or pockets are formed along the slider 130, including a first slot or pocket 136, a second slot or pocket 138, and a third slot or pocket 140. By example, the first slot 136 is disposed between the second and third slots 138 and 140. A first divider or rib 142 separates the first and second slots 136 and 138. A second divider or rib 144 separates the first slot 136 from the third slot 140.

A biasing means 148, such as a coil spring, is mounted within the third slot 140 as well as being seated against a first stop 150 carried on the first housing portion 114, and the divider or rib 144. A second stop 152 also carried on the first housing portion 114 and axially spaced from the first stop 150 toward the first end 118 of the housing 112, as will be described hereafter.

Preferably, the first and second stops 150 and 152 are integrally molded in the first housing portion 114 and project into the internal bore formed in the first housing portion 14 so as to extend into close proximity, while still being spaced from the slider 130. The first and second stops 150 and 152 function to limit the amount of bidirectional sliding movement of the slider 130, as described hereafter, by acting as a seat against which the biasing means or spring 148 is compressed.

Figure 5:
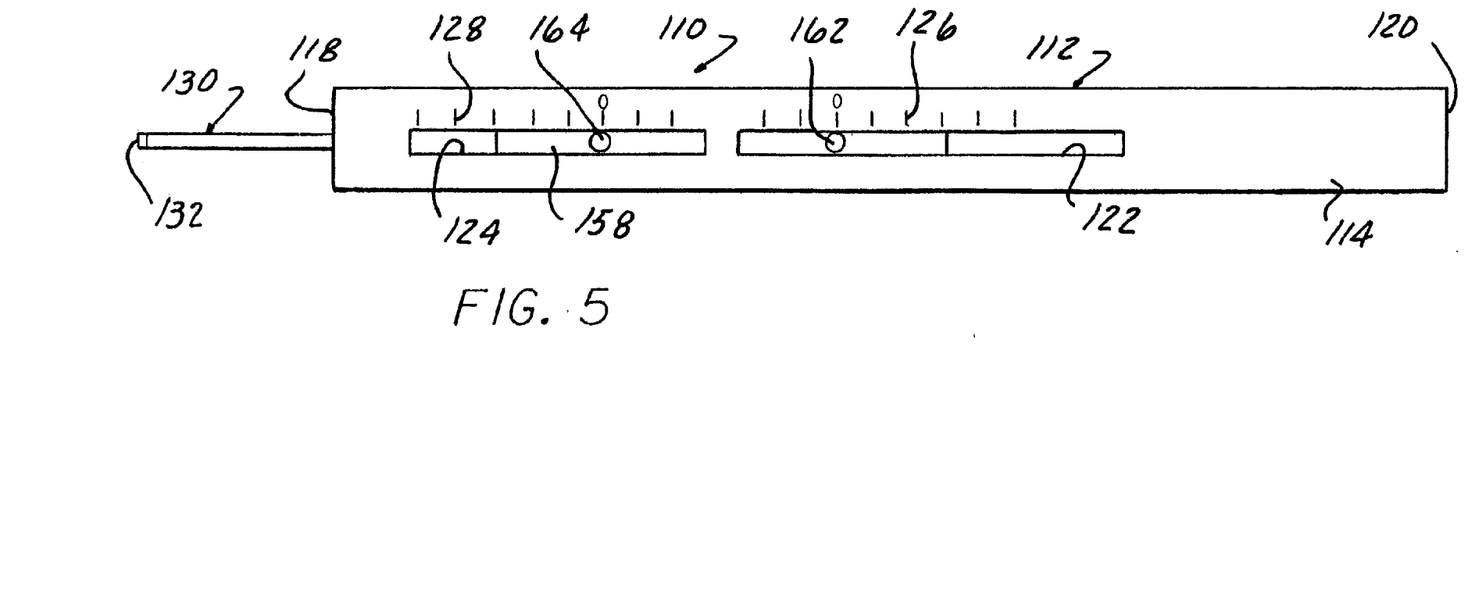
FIG. 5 is a side elevational view of a jaw contact tester according to the second aspect of the present invention.
Figure 6:
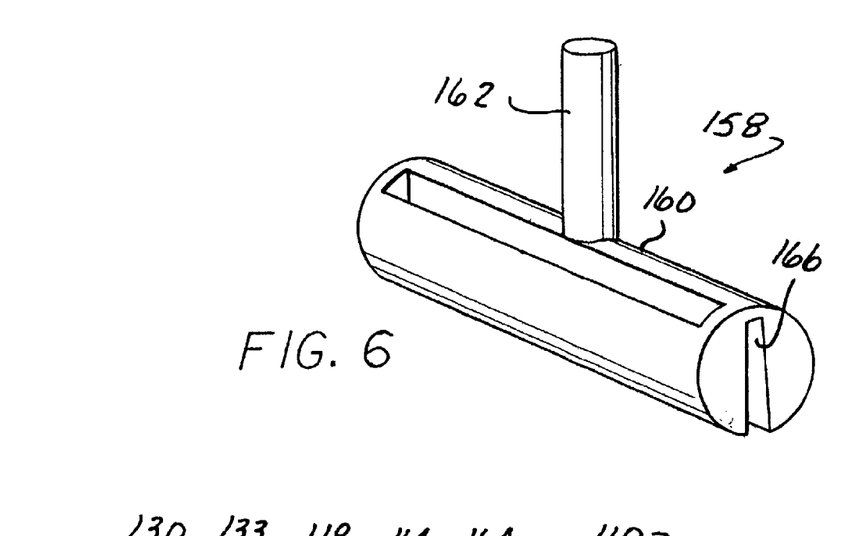
FIG. 6 is an exploded, perspective view of the jaw contact tester as shown in FIG. 5.

First and second sliding members or plungers 156 and 158, respectively, are freely mounted in the first and second slots 136 and 138, respectively. The first and second plungers 156 and 158 are identically constructed and, as shown for the first plunger 156 in FIG. 6, are formed of a generally cylindrical body 160 with an indicator pin 162 carried thereon and extending generally perpendicularly from a central portion thereof The indicator pin 162 is positioned to extend through the first slot 122 in the first housing portion 114, shown in FIG. 5, to provide an indicator in conjunction with the first scale 126. The second plunger 158 has an identical second indicator pin 164 extending therefrom as also shown in FIG. 5. The second indicator pin 164 slides within the second slot 124 to provide a force indication dependent upon the amount of movement of the second plunger 158 relative to the second scale 128.

The first and second plungers, such as the first plunger 156, each have a centrally located, axially extending slot 166 formed in the cylindrical body 160. The slot 166 has inward angled sidewalls which cause the opposed sides of the cylindrical body 160 to be urged slightly outward thereby providing a resistance to free sliding movement of the first plunger 156 within aperture 126 in the first housing portion 114. However, the force exerted on the slider member 130 by the spring 148 is sufficient to overcome this resistance to enable sliding movement of the first plunger 126 or sliding movement of the second plunger 158 as described hereafter.

Figure 7:
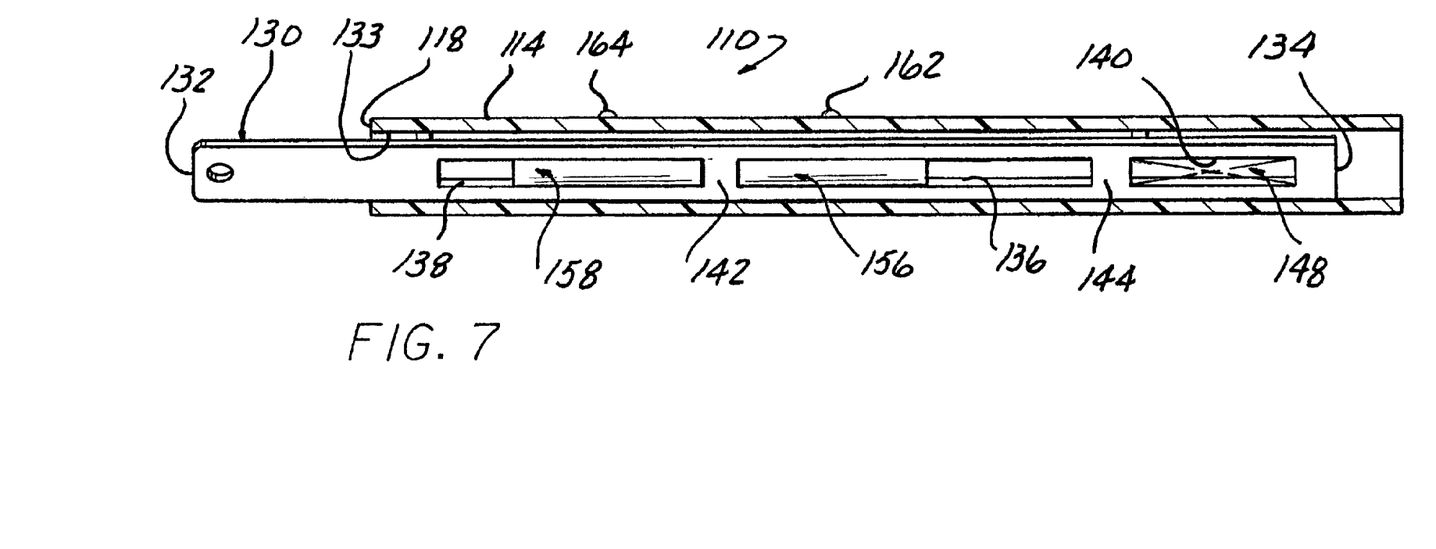
FIGS. 7–11 are side elevational views, with one of the housing portions removed, depicting the operational sequence of the jaw contact tester shown in FIG. 5.

The operational sequence of the jaw contact tester 110 of the second embodiment of the present invention will now be described in conjunction with FIGS. 7–11. FIG. 7 depicts the position of the slider 130, the first and second plungers 156 and 158 and the biasing means or spring 148 in their normal, at rest position as would occur when the jaw contact tester 110 is fully disengaged and spaced from a jaw contact in an electrical device, such as a watthour meter socket or watthour meter socket adapter, not shown.

Figure 8:
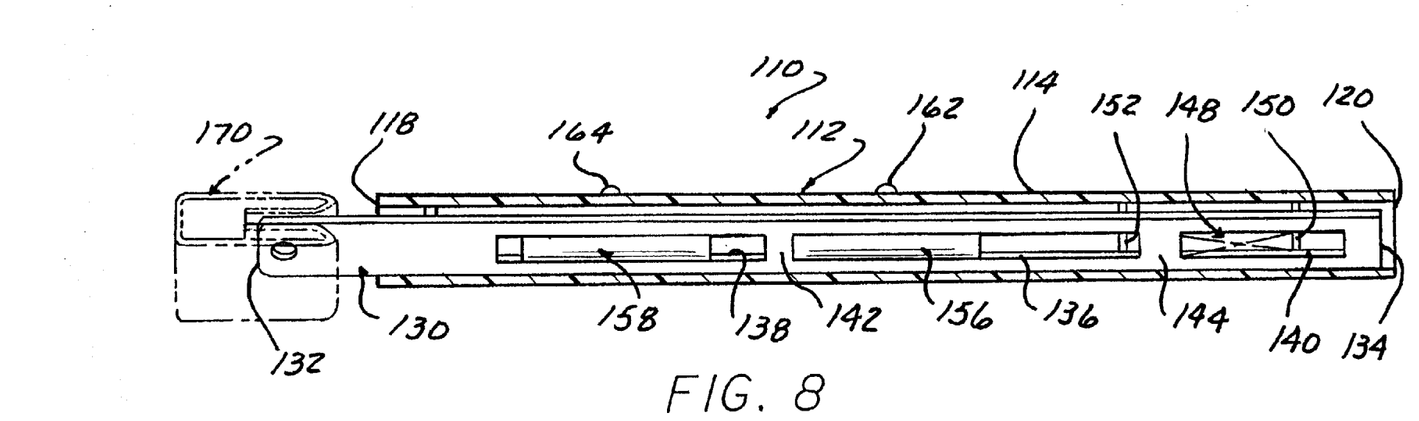
Figure 9:
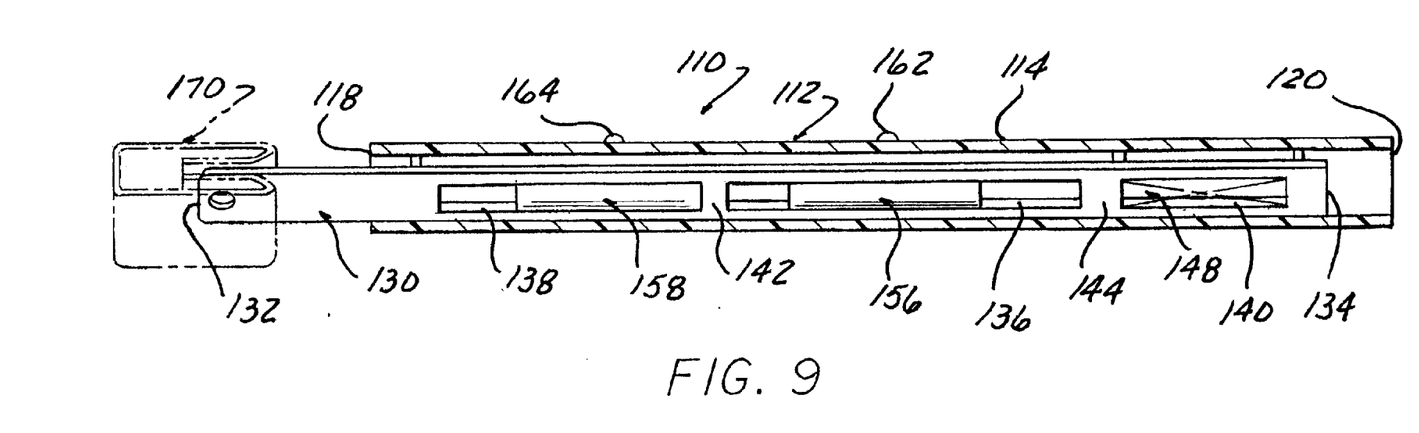

In this normal, at rest position, the first plunger 156 is seated in engagement with the first divider 142 in the slider 130. The second plunger 156 is also seated in contact with the first divider 142. The spring 148 is fully extended in the third slot 140 thereby slidingly biasing the slider 130 such that the first end 132 of the slider 130 extends outward from the first end 118 of the housing 112. The second end 132 of the slider 130, which is shaped as a conventional watthour meter socket or socket adapter blade terminal, is thus positioned for insertion into a jaw contact 170, as shown in FIG. 8. It will be understood that although a conventional folded over jaw contact 170 is shown in FIG. 8, the jaw contact tester 110 is useable with any jaw contact structure normally employed in electrical apparatus, and, in particular, electrical watthour meter sockets and watthour meter socket adapters.

In FIG. 8, the first end 132 of the slider 130 is depicted as being inserted into full engagement with a jaw contact 170. Since the jaw contact 170 has resistance to such insertion, commonly known as "push-in resistance or push-in force", a force exerted on the housing 112 in a direction to urge the first end 132 of the slider 130 into the jaw contact 170 will cause the slider 130 to move internally within the housing 112 in a direction toward the second end 120 as shown in FIG. 8. This sliding movement compresses the spring 148. At the same time, the sliding movement of the slider 130 toward the second end 120 of the housing 112 causes a similar movement of the first plunger 156 toward the second end 120 of the housing 112 through its engagement with the first divider 142 in the slider 130. This movement of the first plunger 156 causes a like movement of the first indicator pin 162 relative to the first scale 126 shown in FIG. 5 to provide an indication of the total push-in force exerted by the jaw contact 170 against insertion of the end 132 of the slider 130. It should also be noted that during the movement of the slider 130 toward the second end 120 of the housing 112, the second plunger 158 remains stationary with the housing 112 as it is disengaged from the first divider 142 and the second end portion of the slider 130.

When the second end 132 of the slider 130 is fully inserted into the jaw contact 170, the spring 148 expands against the second end 134 of the slider 130 and the second divider 144 causing a sliding movement of the slider 130 toward the first end 118 of the housing 112 to reposition the slider 130 for subsequent operation. During such sliding movement of the slider 130 toward the first end 118 of the housing, the first plunger 156 disengages from the first divider 142 and the second divider 144 and remains in a stationary position relative to the housing 112 such that the first indicator 162 remains at the push-in force indication position relative to the first scale 126 as described above. However, the first divider 142 will re-engage the previously stationary positioned second plunger 138 as in the nominal rest position shown in FIG. 7.

Figure 10:
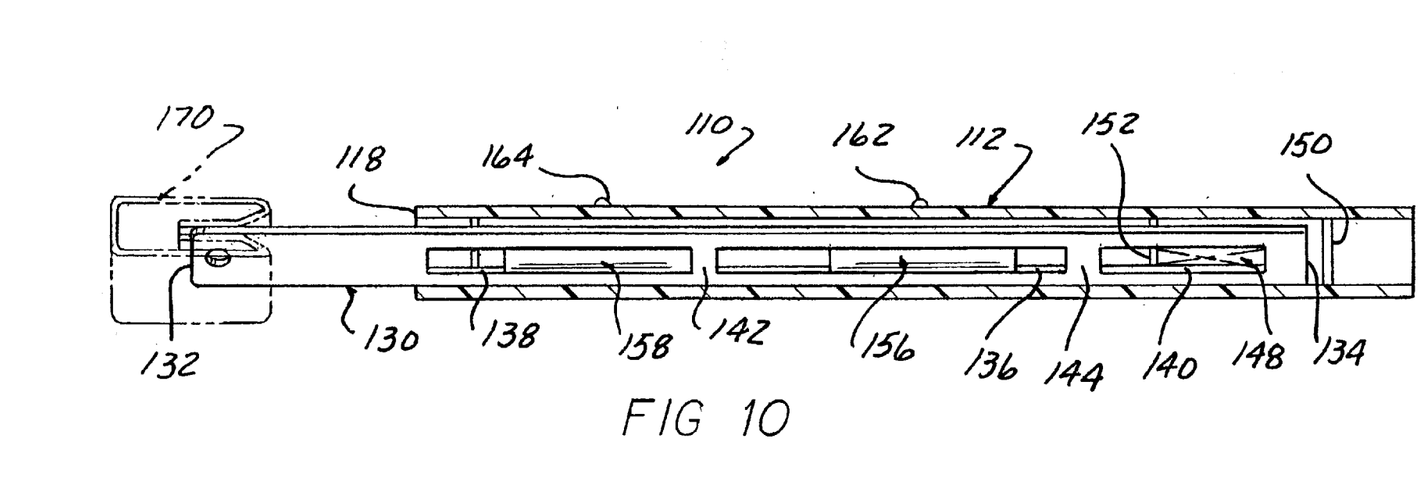
Figure 11:
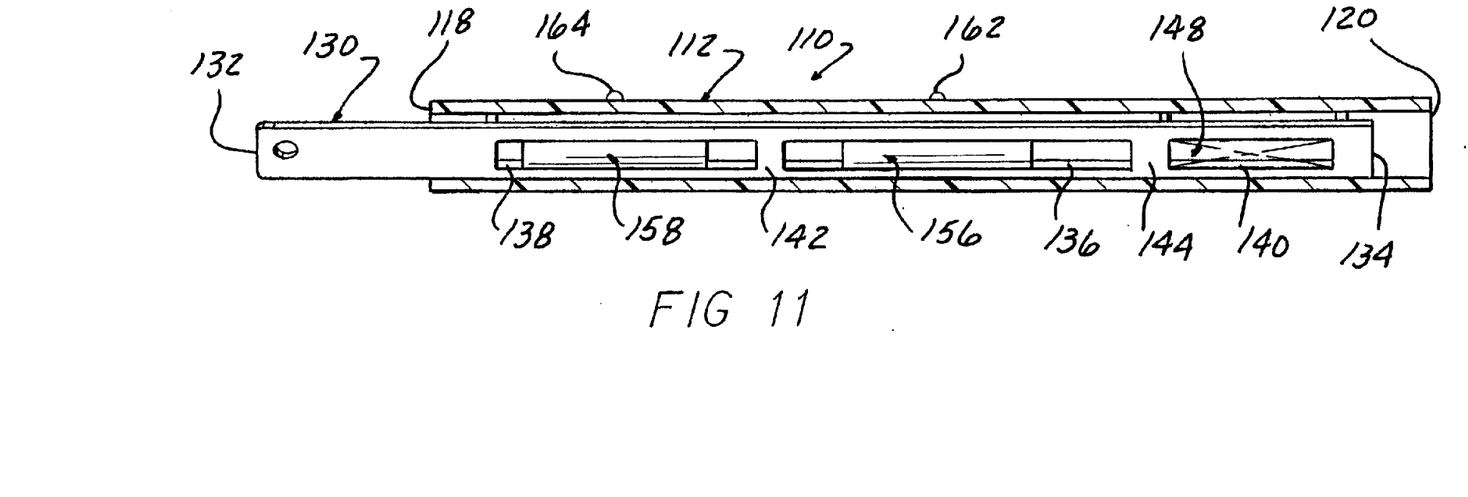

In FIG. 10, a pull-out force tending to separate the slider 130 from the jaw contact 170 is exerted on the housing 112. This causes relative movement of the housing 112 away from the jaw contact 170 and causes a telescoping extension of the housing 112 relative to the slider 130 which is temporarily held stationary with the second end 132 in the jaw contact 170.

The movement of the slider 130 causes the first divider 142 to slide the second plunger 138 toward the first end 118 of the housing 112 thereby moving the second indicator 164 along the second scale 128 to an position consistent with the pull-out force exerted by the jaw contact 170 on the second end 132 of the slider 130. The slider 130 continues to move outward from the first end 118 of the housing 112 until the second end 132 of the slider 130 separates from the jaw contact 170.

Upon release of the second end 132 of the slider 130 from the jaw contact 170, the spring 148 which was previously compressed between the second end 134 of the slider 130 and the second stop 152 during movement of the slider 130 toward the first end 118 of the housing 112, as described above and shown in FIG. 9, re-expands urging slider 130 toward the second end 132 to the second end 120 of the housing 112. This movement separates the first divider 142 from the second plunger 138 thereby enabling the second plunger 130 to remain in a stationary position relative to the housing 112 during further movement of the slider 130 to a nominal rest position shown in FIG. 11. During such movement, the first plunger 138 also remains stationary relative to the housing 112 within the first slot 122. At this time during the operation of the jaw contact tester 110, the first and second indicators 162 and 164 are in their force indicating positions respectively indicating the amount of push-in and pull-out force required to engage the second end 132 of the slider 130 in the jaw contact 170 and to disengage the second end 132 of the slider 130 from the jaw contact 170.

To reset the jaw contact tester 110 for testing another jaw contact, the first and second indicators 162 and 164 are merely urged together until the respective first and second plungers 136 and 138 engage the first divider 142 in the slider 130 and assume the nominal reset position shown in FIG. 7.

The jaw contact tester 110 according to the second aspect of the present invention provides a dual jaw contact test in that it provides an indication of the push-in force required to insert a blade terminal into a jaw contact as well as providing an indication of the pull-out force required separate a blade terminal from a jaw contact.

Figure 12:
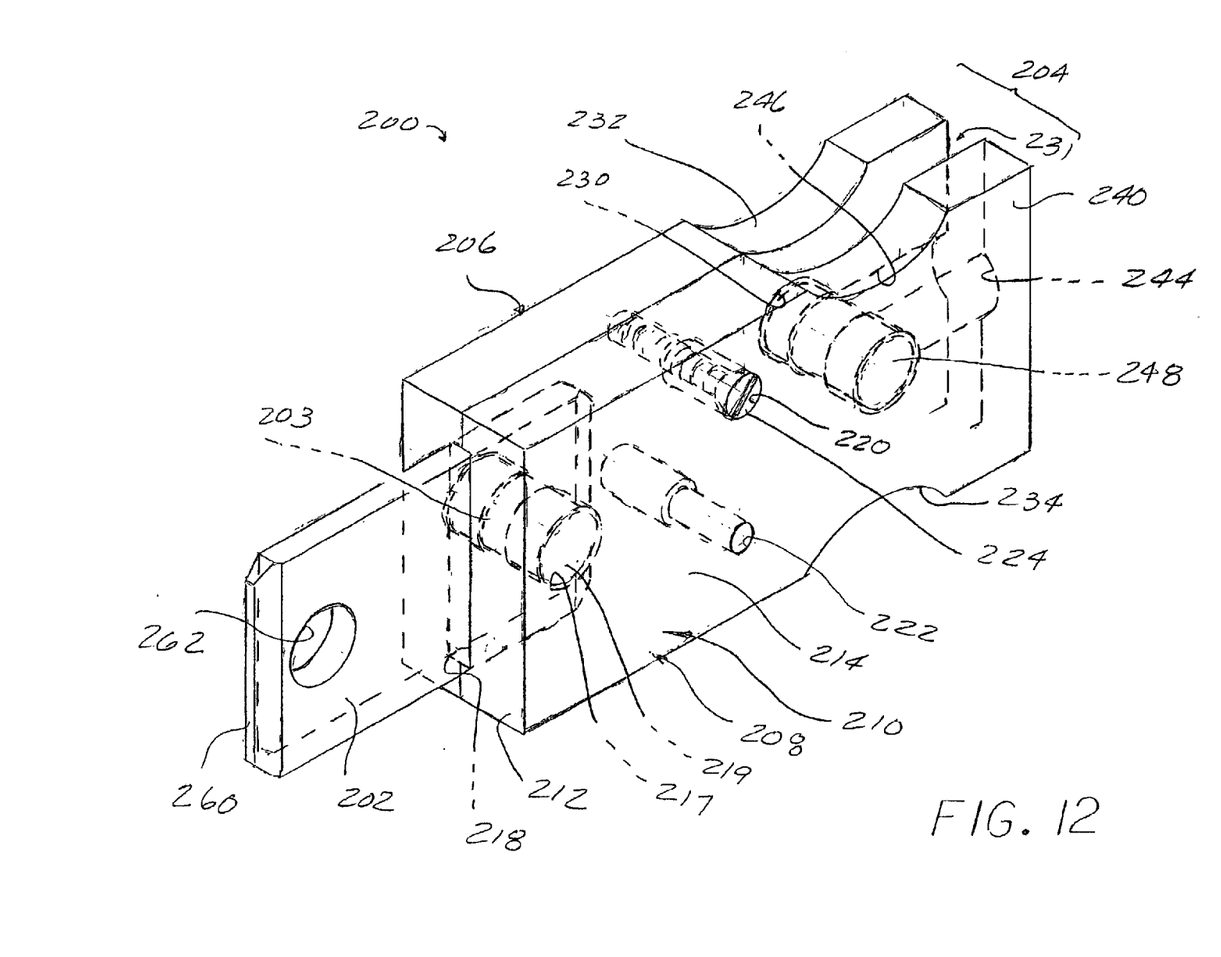
FIG. 12 is a perspective view of another aspect of a jaw contact tester and conditioner according to the present invention.
Figure 13:
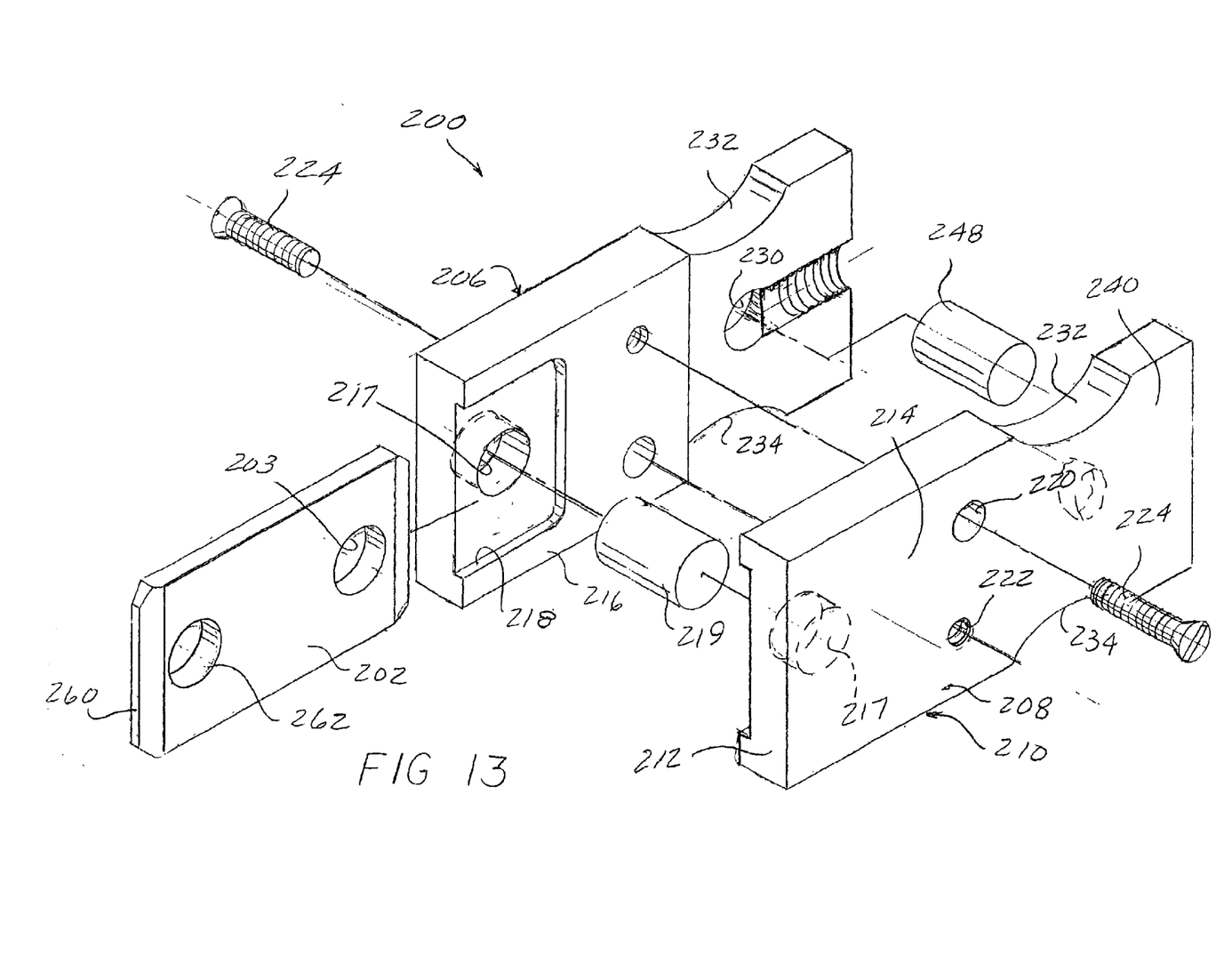
FIG. 13 is an exploded, perspective view of the jaw tester and conditioner shown in FIG. 12.

Referring now to FIGS. 12–15 there is depicted yet another aspect of a jaw contact tester and the jaw conditioner 200 which includes a blade 202 and a blade holder 204. The blade holder 204 is in the form of a body, such a two piece body formed of first and second members 206 and 208, respectively. The first and second members 206 and 208 are identically constructed and mounted in an opposed manner as shown in FIGS. 12 and 13. Alternately, the body 204 could be formed of a single piece construction from a molded material, such as a molded plastic. Any suitable plastic may be employed to form the body 204, with PVC being one example.

As each body member 206 and 208 is identically constructed, only the construction of one body member 208 will be described in detail hereafter. As shown in FIGS. 12–15, the body member 208 includes a head 210 having a generally polygonal cross-section. The head 210 has a first end 212 and opposed first and second surfaces 214 and 216, respectively. A recess 218 is formed in the second surface 216. The recess 218 typically has a polygonal cross-section complimentary to the polygonal cross-section of one end of the blade 202.

Assembly bores 220 and 222 are formed through the head 210, generally at a portion opposite from the first end 212.

The bores 220 and 222, when aligned with the corresponding bores in the opposed body member 206, provide through bores through the body 204 which receive threaded fasteners 224, one extendable through the enlarged diameter end of each bore 220 formed in one of the body members 206 or 208 as shown in FIG. 13.

A closed end bore 217 is formed in the head 210 extending from an inner surface of the recess 218. One end of the bore 217 opens to the recess 218. The bores 217 in each body member 206 and 208 are alignable for receiving a pin or dowel 219 which is insertable through an aperture 203 formed in the blade 202 for securing the blade 202 in the body 204 when the body elements 206 and 208 are fixedly joined together by the fasteners 224.

A stem 230 projects from the head 210. A pair of opposed finger grip surfaces 232 and 234 are formed on opposite sides of the stem 230 to facilitate gripping and handling of the body 204.

As shown in FIG. 14, the thickness of the stem 230 as measured between the opposed surfaces of the body member 208 is smaller than the width of the first end 212 of the head 210. This forms an open ended slot between the opposed stems 230 on the body members 206 and 208 when the body members 206 and 208 are joined together by the fasteners 224 as shown in FIG. 14.

A tail 240 extends from the stem 230 and terminates in a second end 242. The tail 240 has the same thickness as the stem 230 to provide a constant width slot 231 between the opposed stems 230 and the tails 240 when the body members 206 and 208 are joined together.

Two intersecting bores are formed, by example only, in the tail 240 and the stem 230. A first bore 244 projects transversely to the cross-section of the tail 240 and has a closed inner end and an open outer end. The first bore 244 is located in the stem 230. The first bore 244 opens to the opposed body member 206 or 208 and receives a pin or dowel 248. A second bore 246 is formed in each tail 240 and projects from the second end 242 to the first bore 244. The second bore 246 is threaded to receive a threaded connector as described hereafter.

As shown in FIG. 14, when the body members 206 and 208 are joined together, the pin 248 spans the slot 231 formed between the opposed stems 230 and the tails 240 of the body members 206 and 208.

The blade 202 is formed of a high strength material, such as stainless steel. The blade 202 has a shape complimentary to a conventional watthour meter blade terminal to simulate the engagement of the meter blade terminal with a socket or socket adapter jaw contact. The first end 260 and the opposed second end 261 of the blade 202 has tapered side edges for easier insertion into a jaw contact. A second aperture 262 is formed in the blade 202 adjacent to the first end 260.

In assembling the jaw tester 200, the two identically constructed body members 206 and 208 are positioned in an opposed, inverted manner with respect to each other such that the surfaces 216 of the head portions 210 face each other. The pins 219 and 248 are inserted respectively into the bores 217 and 244 in one of the body members, such as body member 206. The aperture 203 in the blade 202 is mounted over the pin 219 to seat the pin 219 in one recess 218, such is the recess 218 in the body member 206. The opposed body members 206 and 208 are then urged together with the pins 219 and 248 respectively engaging the bores 217 and 244 in the opposed body member 208. The fasteners 224 are then inserted through opposite body members 206 and 208 in opposite bores 220 in the body members 206 and 208 to secure the body members 206 and 208 into a secure, unitary body 204. As noted above, in this assembled position, the stems 230 and the tails 240 of the body members 206 and 208 are spaced apart to define the narrow slot 231 extending axially inward from the second end 242 of the body 204.

The blade 202 has a constant cross-section between opposed ends 260 and 261. This enables the blade 202 to be reversed in the body 204 when one end 260 of the blade 202 becomes worn through repeated insertions and removal sequences from jaw contacts.

Figure 15:
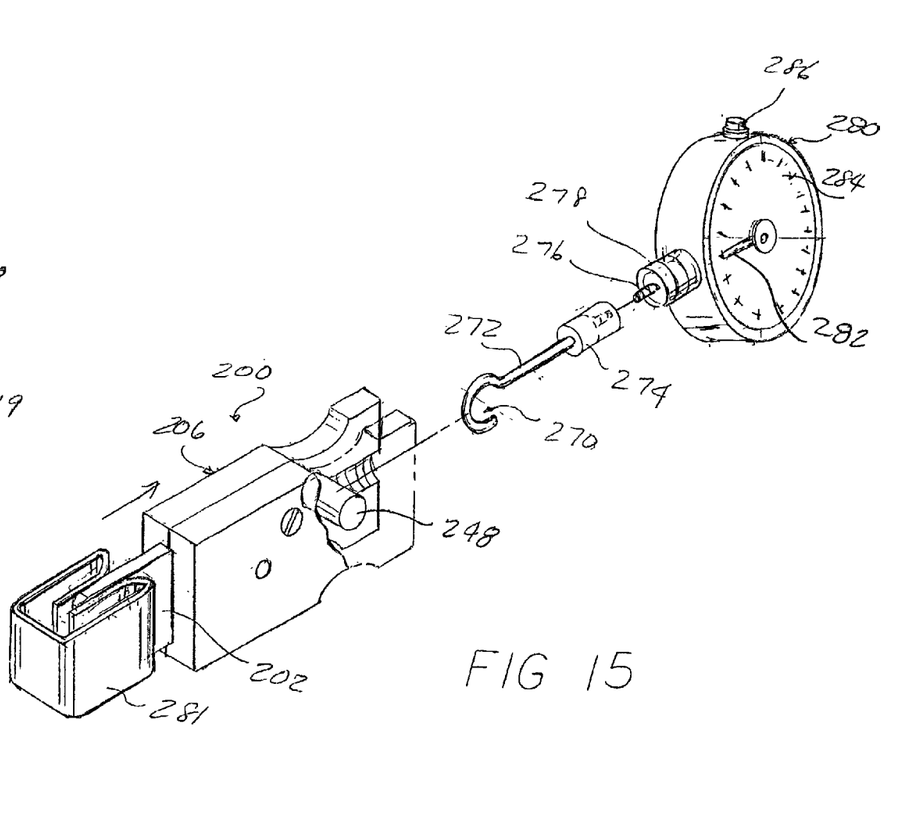
FIG. 15 is an exploded, perspective view showing the use of the jaw contact tester and conditioner shown in FIGS. 12–14 with a folded jaw contact and a force measurement gauge for measuring jaw pull-out forces.

As shown in FIG. 15, the pin 248 mounted between the tails 40 of the two body members 206 and 208 is engagable with a hook 270 formed at one end of an elongated stem 272 mounted in a coupler 274 which has an internally threaded bore extending from an opposite end. The threaded bore is adapted for receiving a threaded fastener 276 mounted on one end of a coupler 278 attached to a force measurement device or gauge 280, such as a force measurement gauge sold as the Force Dial, Model Number FDK60 by the Wagner Company. The gauge 280 is capable of measuring force in a suitable unit of measure, such as pounds, applied to a moveable plunger internally connected to the coupler 278.

In order to measure the pull-out force of a particular jaw contact, the blade 202 of the tester 200 is first inserted into the jaw contact 281. As shown in FIG. 15 the user, after resetting the moveable indicator or needle 282 to a zero setting on the scale 284 by depression of a reset pushbutton 286 on the gauge 280, exerts a pull-out force through the hook 270 to the jaw contact tester 200. The gauge 280 will read the maximum amount of force required to separate the blade 202 from the jaw contact 281.

Figure 16:
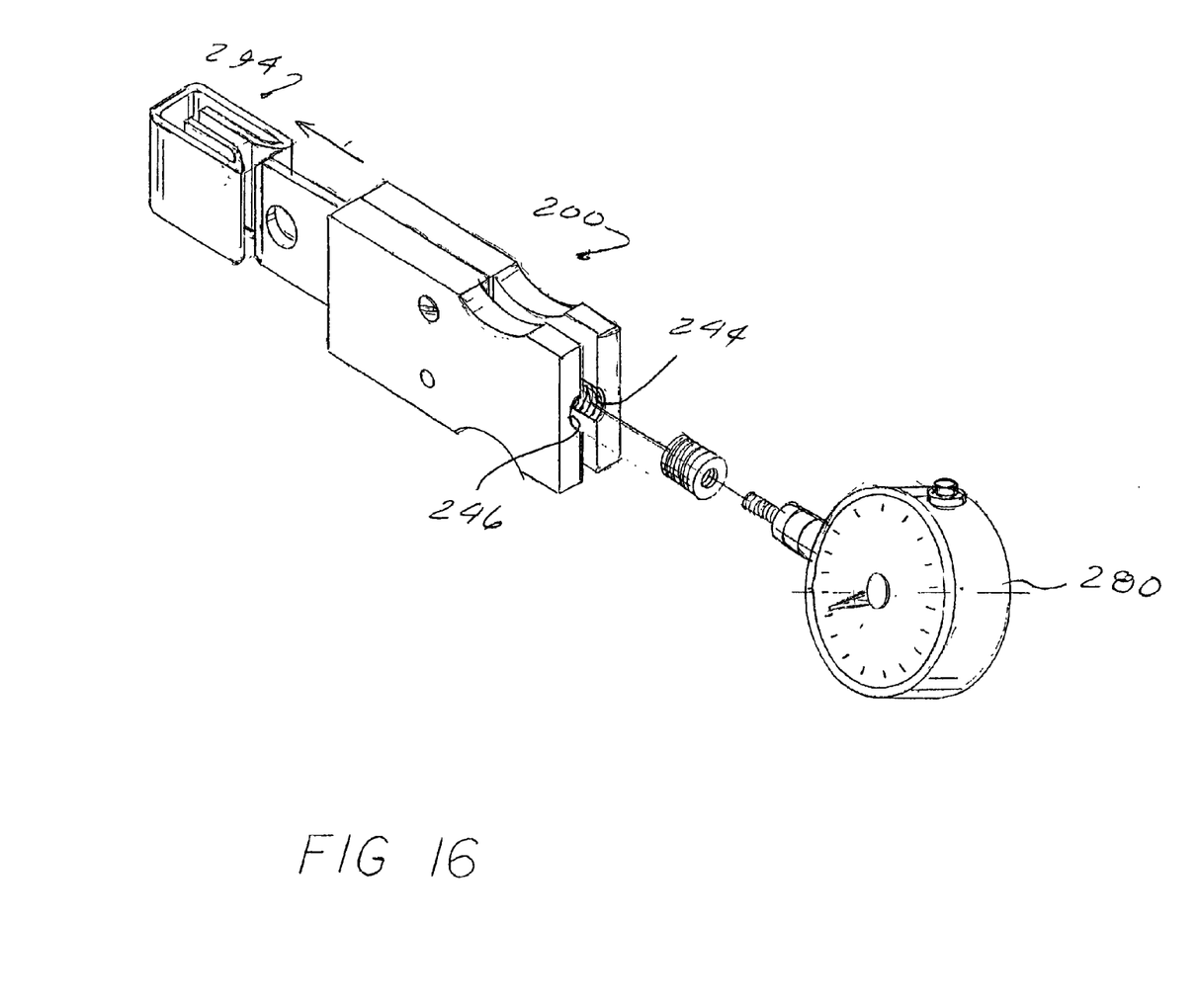
FIG. 16 is an exploded, perspective view of the jaw contact tester shown in FIGS. 12–14 with a folded jaw contact and a force measurement gauge measuring jaw push-in forces.

Push-in force can be measured by using the same gauge 200, but with a different coupler 290 shown in FIG. 16. The coupler 290 is in the form of a cylindrical pin having a bore 292 which receives the fastener 276 on the coupler 278 attached to the gauge 280. At least the exterior surface of one end 294 of the pin 290 is threaded so as to be threadingly received in a threaded bore formed by the opposed bores 246 in the body members 206 and 208 of the jaw contact tester 200. With the coupler or pin 290 threadingly inserted into the jaw contact tester 200, the user can exert a push-in force to forcibly insert the blade 202 into the jaw contact 294. The maximum amount of exerted force will be measured by the gauge 280 and displayed by the angular position of the indicator 282 on the scale 284.

In summary, there has been disclosed a unique jaw contact tester and conditioner for jaw contacts used in watthour meter sockets and socket adapter/extenders which can easily be used with a force measurement device to provide an indication of the jaw contact push-in and pull-out force for blade terminal insertion and removal. At the same time, the jaw contact tester can be used as a conditioner and repeatedly inserted and removed from a jaw contact to precondition the jaw contact for use with the blade terminals of a watthour meter.

What is claimed:

1. A jaw contact test apparatus for testing at least one of a blade insertion force and a blade pull-out force in an electrical power service apparatus having at least one jaw contact receiving a watthour meter blade terminal, the jaw contact test apparatus comprising:
   a body;
   a blade carried on the body; and
   a force measurement indicator, carried with the body, for providing a value of at least one of an applied insertion force required to insert the blade into one jaw contact and an applied pull-out force required to separate the blade from an inserted position in one jaw contact.

2. The jaw contact test apparatus of claim 1 further comprising:
   the body having first and second ends, the blade mounted in the first end of the body with an end portion of the blade extending from the first end of the body; and
   the second end of the body adapted for coupling to the force measurement indicator.

3. The jaw contact test apparatus of claim 1 wherein the body comprises:
   two body members;
   fastener means for joining first and second body members together; and
   a recess formed in one end of at least one of the body members for receiving the blade.

4. The jaw contact test apparatus of claim 3 wherein:
   the two body members are identically constructed and invertingly joined to each other by the fastener means.

5. The jaw contact test apparatus of claim 3 further comprising:
   a bore formed at another end of the body;
   a pin transversely extending across the bore; and
   a hook attachable to the force measurement indicator and the pin to couple the force measurement indicator to the body to measure one of the pull-out force and the insertion force.

6. The jaw contact test apparatus of claim 2 further comprising
   the second ends of each of the first and second body members spaced apart to define a bore at one end of the body;
   a pin transversely extending across the bore; and
   a hook attachable to a force measurement indicator and the pin to couple the force measurement indicator to the body to measure one of a pull-out force and a push-in force.

7. The jaw contact test apparatus of claim 1 further comprising:
   a bore extending from one end of the body; and
   an adapter mountable in the bore and adapted to be connected to a force measurement indicator to couple the force measurement indicator to the body.

8. The jaw contact test apparatus of claim 7 wherein:
   the adapter is threadingly coupled to the bore.

9. A jaw contact test apparatus for testing at least one of a blade insertion force and a blade pull-out force in an electrical power service apparatus having at least one jaw receiving a watthour meter blade terminal, the jaw contact test apparatus comprising:
   a body;
   a blade carried on the body;
   a force indicator, carried with the body, for providing an indication of at least one of an insertion force required to insert the blade into a jaw contact and a pull-out force required to separate the blade from an inserted position in a jaw contact;
   the body having a fixed support extending from one end;
   the blade mounted at one end of the fixed support;
   a housing movably mounted over the blade and the support;
   biasing means, mounted about the blade and seated against the housing, for normally biasing the housing to a first position substantially encompassing the blade; and an aperture formed in the housing allowing extension of an end portion of the blade therethrough;

the force indicator including a biasing means having a pre-determined force constant to provide a predetermined amount of force equal to a predetermined blade pull-out force from a jaw contact, the biasing means overcoming the pull-out force resistance of the jaw contact to disengage the blade from the jaw contact only when the spring force of the biasing means is greater than the pull-out force resistance of the jaw contact on the blade.

10. The jaw contact test apparatus of claim 9 further comprising:

the housing having first and second housing portions, the first housing portion telescoping arranged with respect to the second housing portion;

a slot formed in a first end of the first housing portion; and the biasing means disposed between the first end of the first housing portion and the support fixed to the second housing portion.

11. The jaw contact test apparatus of claim 9 wherein the biasing means comprises a spring.

12. The jaw contact test apparatus of claim 11 wherein:

the spring is replaceable to vary the pull-out force exerted by the biasing means on the support.

13. A jaw contact test apparatus for testing at least one of a blade insertion force and a blade pull-out force in an electrical power service apparatus having at least one jaw receiving a watthour meter blade terminal, the jaw contact test apparatus comprising:

a body;

a blade carried on the body;

a force indicator, carried with the body, for providing an indication of at least one of an insertion force required to insert the blade into a jaw contact and a pull-out force required to separate the blade from an inserted position in a jaw contact;

the body having an aperture at one end;

a slider moveably disposed within the body and having the blade carried at one end, the blade having an end slidable external of the housing and adapted for releasable engagement in a jaw contact;

a first plunger carried by the slider for movement in one direction and displaceable from the slider by movement of the slider in an opposite direction; and biasing means coupled to the slider for biasing the slider in a direction to retract the one end of the slider toward the housing;

the force indicator including a first indicator carried by the first plunger and extending through the aperture in the body adjacent to a scale means carried on the body for indicating a force required to move the blade relative to the jaw contact.

14. The jaw contact test apparatus of claim 13 further comprising:

a second plunger carried in the body; and the force indicator including a second indicator carried by the second plunger and extending through another aperture in the body for displacement relative to a second scale means carried on the body, the second plunger operable by movement of the slider in an opposite direction.

15. A method for measuring one of a blade insertion force into a jaw contact and a blade pull-out force to separate a blade from a jaw contact in an electrical power service apparatus, the method comprising the steps of:

mounting a blade in a body; and coupling a force measurement device to the body for measuring at least one of a blade insertion force into a jaw contact and a pull-out force for disengaging the blade from a jaw contact.

16. The method of claim 15 further comprising the steps of:

forming an open ended slot at one end of the body carrying the blade;

mounting a pin transversely across the slot; and attaching a coupling member between the pin and the force measurement device.

17. The method of claim 15 further comprising the steps of:

forming a threaded bore at one end of a body carrying the blade;

threadingly mounting a coupler in the bore;

attaching the force measurement device to the coupler.

18. A method for measuring one of a blade insertion force into a jaw contact and a blade pull-out force to separate a blade from a jaw contact in an electrical power service apparatus, the method comprising the steps of:

mounting a blade in a body;

coupling a force measurement device to the body for measuring at least one of a blade insertion force and a blade pull-out force;

forming an open ended slot at one end of the body carrying the blade;

mounting a pin transversely across the slot;

attaching a coupling member between the pin and the force measurement device;

mounting a blade to a support in the body;

disposing a housing over the support;

coupling the biasing means between the housing and the body; and providing the biasing means with a spring force to provide a predetermined amount of force equal to a predetermined blade pull-out force from the jaw contact so that the biasing means overcomes the pull-out force resistance of the jaw contact to disengage the blade from the jaw contact only when the spring force of the biasing means is greater than the pull-out force resistance of the jaw contact on the blade.

19. The method of claim 18 further comprising the step of:

varying the force provided by the biasing means by varying the spring force.

20. The method for measuring one of a blade insertion force into a jaw contact and a blade pull-out force to separate a blade from a jaw contact in an electrical power service apparatus, the method comprising:

mounting a blade in a body;

coupling a force measurement device to the body for measuring at least one of a blade insertion force and a blade pull-out force;

forming an open ended slot at one end of the body carrying the blade;

mounting a pin transversely across the slot;

attaching a coupling member between the pin and the force measurement device;

providing a movable slider in the body;

attaching a blade to one end of the slider;

mounting a first plunger on the slider for movement in one direction, the first plunger displaceable from the slider upon movement of the slider in an opposite direction;

providing biasing means coupled to the slider for biasing the slider in a direction to retract the one end of the slider toward the housing;

mounting a force indicator including a first indicator on the first plunger, the first indicator extending through an aperture in the housing; and providing a scale means on the body for indicating a force required to move the blade relative to the jaw contact by the position of the first indicator relative to the scale means.

21. The method of claim 20 further comprising the steps of:

providing a second plunger in the body;

providing the force indicator with a second indicator carried by the second plunger and extending through another aperture in the body, the second indicator displaceable relative to a second scale means carried on the body, the second plunger operable by movement of the slider in an opposite direction from the normal direction of movement provided by the biasing means.

22. A jaw contact test apparatus for testing at least one of a blade insertion force and a blade pull-out force in an electrical power service apparatus having at least one jaw receiving a watthour meter blade terminal, the jaw contact test apparatus comprising:

a body;

a blade carried on the body;

a force indicator, for providing an indication of at least one of an insertion force required to insert the blade into a jaw contact and a pull-out force required to separate the blade from an inserted position in a jaw contact; and means for coupling the force indicator to the body to measure at least one of insertion force and pullout force.

* * * * *